United States Patent [19]
Arbter et al.

[11] Patent Number: 5,820,545
[45] Date of Patent: Oct. 13, 1998

[54] METHOD OF TRACKING A SURGICAL INSTRUMENT WITH A MONO OR STEREO LAPAROSCOPE

[75] Inventors: Klaus Arbter, Landsberied; Guo-Quing Wei, Gilching, both of Germany

[73] Assignee: Deutsche Forschungsanstalt Fur Luft-Und Raumfahrt E.V., Köln, Germany

[21] Appl. No.: 696,159

[22] Filed: Aug. 13, 1996

[30] Foreign Application Priority Data

Aug. 14, 1995 [DE] Germany .................. 195 29 950.7

[51] Int. Cl.⁶ ........................................... A61B 1/04
[52] U.S. Cl. .............................. 600/117; 600/102; 348/65
[58] Field of Search .................... 600/118, 117, 600/102; 382/152–154, 164, 165, 128, 282, 291; 348/71, 65, 169–172

[56] References Cited

U.S. PATENT DOCUMENTS

| | | | |
|---|---|---|---|
| 5,417,210 | 5/1995 | Funda et al. | 600/109 |
| 5,467,127 | 11/1995 | Jong-Pil | 348/169 |
| 5,506,912 | 4/1996 | Nagasaki et al. | 600/103 |
| 5,528,703 | 6/1996 | Lee | 382/128 |
| 5,548,663 | 8/1996 | Sekine et al. | 382/164 |
| 5,557,688 | 9/1996 | Nakamura | 382/164 |
| 5,649,021 | 7/1997 | Matey et al. | 348/65 |

FOREIGN PATENT DOCUMENTS 8706353  10/1987  WIPO .

*Primary Examiner*—John P. Leubecker
*Attorney, Agent, or Firm*—Browdy and Neimark

[57] ABSTRACT

For tracking a mono- or stereo-laparoscope in connection with minimally invasive surgery, where the laparoscope is moved by a robot in respect to surgical instruments located in the operation area, surgical instruments are color-coded and are identified in images provided by the camera of the laparoscope. Signals for controlling the robot are derived from the position of the color-coded surgical instruments in images generated by both cameras. The robot automatically brings the laparoscope into such a position that the color-coded surgical instruments are continuously shown in the center area of the monitor device and hold the laparoscope distance to the surgical instrument in the case of stereo. To prevent interfering movements of an image when working with the surgical instruments, the laparoscope continuously tracks the color-coded surgical instruments in such a way that the tracking of the image is controlled relatively lightly in the central area of the monitor, but strongly in its edge area.

9 Claims, 2 Drawing Sheets

METHOD OF TRACKING A SURGICAL INSTRUMENT WITH A MONO OR STEREO LAPAROSCOPE

FIELD OF THE INVENTION

The invention relates to a method for tracking a mono- or stereo-laparoscope in connection with minimally invasive surgery.

BACKGROUND OF THE INVENTION

A method for performing operations is known from WO 87/06353, wherein a moving object present in a monitored room is detected by means of two cameras. The method merely determines the space coordinates of marked points.

Minimally invasive surgery is gaining increased importance as an alternative to open surgery. It is already employed today in many hospitals in routine operations, for example the resection of the gall bladder. Up to now the camera guidance was performed by an assistant surgeon in cases where the surgery is performed laparoscopically in connection with an electronic image transmission to a monitor.

However, such camera assistance is subject to a number of problems. The camera guidance can become unsteady because of the operator becoming tired and his or her concentration being reduced. Furthermore, instructions from the operating surgeon are misinterpreted time and again. In addition, independent actions by the assisting surgeon, which interfere with the course of the surgery, can quite often result in hard feelings between the operating surgeon and the assistant. The surgeon may feel psychologically hampered. Also, the job of camera assistant does not require the high-quality medical training of an assistant surgeon, so that it is basically too highly paid; and young doctors understandably do not like to do it.

Holding devices which can be quickly removed and fixed in place have been used in guidance systems employed up to now. Examples of these are multi-link arms with ball and socket joints and joint locks, as well as the so-called "C bow" and a "scissors joint" of KFK-Karlsruhe. Furthermore, a robot with six degrees of freedom developed particularly for laparoscopic use is sold by the Computer-Motion company, which is equipped with a manual operating device as well as with a foot switch for controlling the operation.

Although the known holding devices relieve the assistant surgeon of physical stress, they still have the disadvantage that they do not make a camera assistant unnecessary. This also applies, analogously, to the manually operated robot. Although the robot control can be operated by the surgeon himself by means of a foot switch, its operation distracts the surgeon from the actual surgical work.

SUMMARY OF THE INVENTION

Accordingly, the present invention has an object, among others, to overcome deficiencies in the prior art such as noted above.

It is therefore the object of the invention to create a method for tracking a mono- or stereo-laparoscope in connection with minimally invasive surgery in which, on the one hand, an assistant surgeon is no longer necessary for tracking with a camera and, on the other hand, the operating surgeon is also relieved of additional control work, such as controlling a robot.

In accordance with this and other objects apparent from the following description, the invention provides a method for tracking a mono- or stereo-laparoscope in connection with minimally invasive surgery.

In accordance with a preferred embodiment of the invention, the surgical instruments are color-coded so that they can be identified by the image provided by one laparoscopy camera. In accordance with the invention, signals for controlling the robot are then derived from the position of the color-coded surgical instruments in the image generated by the laparoscopy camera. By means of evaluating this signal, the robot is then capable of automatically placing the laparoscope into such a position that the color-coded surgical instruments are continuously shown in the central area of the observing monitor. In addition, if a stereo-laparoscope having two cameras is used the distance between the laparoscope head and the surgical instrument can also be controlled automatically.

Thus, the method of the invention makes it possible for an appropriately controlled robot to align the cameras of a stereo-laparoscope automatically with the surgical instruments as soon as the operating surgeon issues a command to do this.

The position of the camera in relation to the surgical instruments is thus determined according to the invention and in case of a possible misalignment the camera(s) automatically track(s) with the aid of the robot. The camera signals, which are provided anyway, are used for this and by means of them the surgical instruments or the markings on the surgical instruments are identified by means of the applied color.

With the invention the signal source therefore is a marker or a marking in a suitable color, which is applied or provided in the vicinity of, or on the tip of, an instrument. The realization of this signal source is extremely simple and its cost negligible. In addition, every existing set of surgical instruments can also be provided with appropriate color marks later (i.e. retro-fitted), so that the object of the invention can also be employed extremely economically in respect to already existing, highly valuable surgical instruments.

Furthermore it is also possible to embody the handle of an instrument, which as a rule was black up to now, in a suitable color. In this case the application of a marker could be omitted.

On top of everything, such a signal source does not need space and it also does not affect the mechanical structure or the design of the instruments in any way. In the same way, an applied marking or applied marker does not interfere with the manipulation of the surgical instruments.

This type of signal source, in the form of a colored marking, also does not require a special energy source, which is particularly advantageous because of the fact that, in any event, light supplied from the outside is urgently needed by the surgeon.

Coding of the instruments can also be carried out by the provision of different colors, so that it is possible to apply the method in accordance with the invention selectively to different instruments. A color differentiation in video images can be quickly and cost-effectively realized by means of modern image processing devices.

The method in accordance with the invention is furthermore designed in such a way that it can be realized with the aid of commercially available devices and components. The method of the invention operates in real time, and a high degree of safety in actual use is also dependably assured.

Thus, by means of the method in accordance with the invention an operating surgeon is given a very comfortable and reliable method for guiding the laparoscope without having to lay the laparoscopy instrument aside. In accordance with a preferred embodiment of the invention the laparoscope always follows the color-coded surgical instruments in the so-called "continuous model". In this case the control is laid out in such a way that it acts only weakly in the central image area and strongly in its edge area. By means of this it is also assured that no interfering image movements occur during work in the operating area, for example when incising tissue. On the other hand it is also assured that the surgical instruments are not lost in the monitor image because of larger movements.

The above and other objects and the nature and advantages of the present invention will become more apparent from the following detailed description of preferred embodiments taken in conjunction with drawings, wherein.

DETAILED DESCRIPTION OF THE PREFERRED EMBODIMENTS

First, the components used for executing the method in accordance with the invention will be described.

Commercially available stereo-laparoscopes have a rigid tube with a diameter on the order of magnitude of 10 mm. On the end which is to be inserted into the site of the operation, a lens is provided if it is a mono-laparoscope, and two lenses are provided if it is a stereo-laparoscope. At the other end is a camera head into which one and two CCD cameras respectively have been integrated. The image provided by the camera(s) are available as video signals, for example in the RGB signal format.

A robot with an appropriate robot control, for example from the Computer-Motion company, Goleta, Calif., USA, has six degrees of freedom, two of which are passive. By means of this the danger of injury to the patient by lateral forces, i.e. forces which extend transversely in respect to the laparoscope axis, is avoided. In this case a library is available for controlling such a robot, the preset commands move left(speed), move right(speed), move up(speed), move down (speed), zoom in(speed) and zoom out(speed) refer to the movements of an image on a monitor and generate the required control sequences for the robot joints.

Furthermore, a commercially available video color digitizer, for example from the firm DataCube, Inc., Danvers, Mass., USA, is used for digitizing the recorded analog video signals. Such a digitizer has a multiplexer on the analog side, by means of which it is selectively possible to switch back and forth between two cameras, and on the digital side it has a module for color space conversion.

In addition, a so-called pipeline processor for real time image processing, such as is offered by the DataCube company for example, is connected with a digitizer, such as the one from the DataCube company, by means of a 10 MHz data bus. A look-up table (LUT), stabilizing processors, a convolution module and additional modules are, for example, contained in such a processor. Such a processor has the required modules for image storage and processing; user- or use-specific initialization of this processor; and its wiring can be programmed. A central unit (CPU) is simultaneously used for administering the image processing hardware and as an interface for the robot control.

Figure 1:
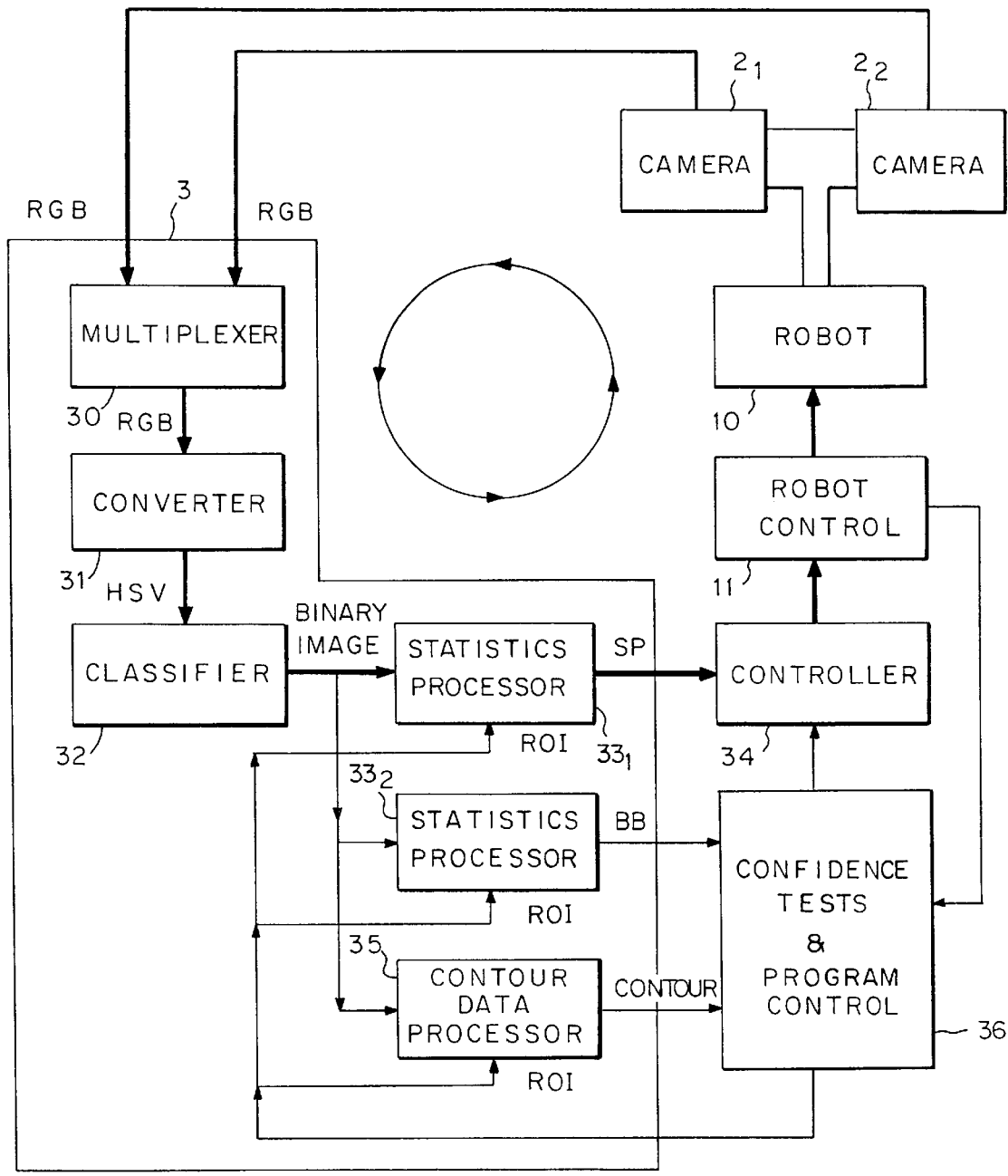
FIG. 1 is a schematic block diagram of a device for executing the method in accordance with the invention.

As can be see from FIG. 1, the basic structure for executing the method in accordance with the invention is a control loop. A robot 1 holds a laparoscope, of which only the two CCD cameras $2_1$ and $2_2$ are represented in FIG. 1. The camera is optional for lateral control. Images recorded by means of the cameras $2_1$ and $2_2$ are transmitted in the RGB (red-green-blue) format to an image processing unit 3. The images present in the RGB format are applied to a multiplexer 30 of the image processing unit 3, which optionally switches back and forth between the two cameras $2_1$ and $2_2$ in a preset sequence of 25 Hz, for example, so that stereo images can be evaluated with only one image processing unit.

However, it is intended that such image processing should differentiate pixels which come from a color marker or marking of a laparoscope (not represented in FIG. 1) and all the other pixels of the scene. Furthermore, the HSV (hue-saturation-value) color space is considerably better suited for a classification than the RGB color space, because in the HSV color space the color is represented by the two components "H" and "S", which are independent of intensity, and by the component "V", which is independent of color. For this reason an RGB–to–HSV color space conversion takes place in a converter 31 downstream of the multiplexer 30.

Thus, the converter outputs a data stream including pixels from both camera images. Data words of the data stream correspond to the hue and saturation of the pixels.

Figure 2:
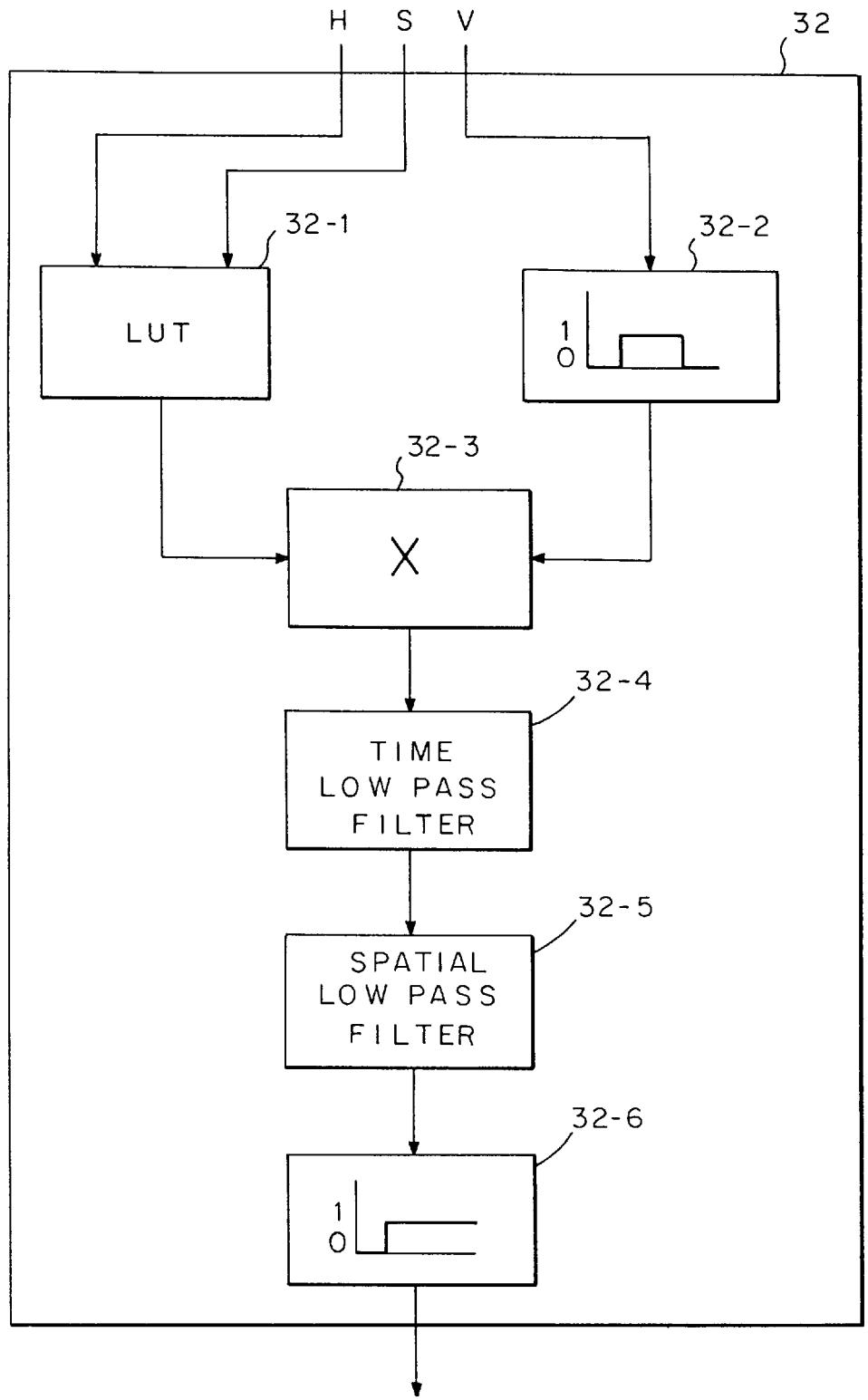
FIG. 2 is a block circuit diagram of a classifier used in the device in FIG. 1.

A classifier 32 is connected downstream of the converter 31, whose particular structure will be described below in reference to FIG. 2. In FIG. 2, the central component of the classifier 32 is a (16×16) bit look-up (LU) table 32. A 16-bit word is formed from respectively 8 bits of the color components "H" and "S" and is used as the address for the LU table 32-1. In this case the LU table 32-1 is pre-allocated in such a way that color values which are part of a marker receive the highest logical value of 255 (logical "1"), while all others receive the value zero (logical "0"). The LU table can be read at a rate of 20 MHz.

Erroneous classifications can occur because of camera noise and saturation effects, causing marker pixels to be erroneously included with non-marker pixels, or vice versa. This danger is particularly great at a low signal level. For this reason the classification results obtained by means of the LU table are post-treated with the aim of correcting all pixels which were erroneously marked with the value 255 (those classified as marker pixels). It is acceptable in this case that pixels which are part of a color marker or marking are also given the value zero.

All those pixels, which because of noise were assigned to a very low signal level or because of saturation to a very high signal level, are set to zero with the aid of the signal component "V". To this end the signal component "V" is passed through the bidirectional threshold value generator 32-2 and is multiplied with the output signal of the LU table 32-1 in a multiplication unit 32-3.

The remaining residual errors are individual pixels or small groups of pixels in rapidly changing locations. In contrast, the marker image (the useful signal) is an extended area which moves very slowly. Based on this difference in the spatial and time behavior of the actual marker signal and the spurious signals, it is therefore possible to drastically reduce residual errors very efficiently by means of time and subsequent spatial low-pass filtering in a time low-pass filter 32-4 and a spatial low-pass filter 32-5 connected downstream of it. Following these, an appropriate threshold value operation is performed in a unidirectional threshold value generator 36-2, by means of which efficient non-linear filtering is realized.

If filtering is performed by the addition of sequential frames and convolution with an evenly allocated mask, for example of the size (7×7), an error reduction by factors between 50 to 100 per classification error is achieved.

A subsequent statistical evaluation in a statistics processor $33_1$ downstream of the classifier provides the marker image center (SP). An additional statistics processor $33_2$, provided in parallel with processor $33_1$, finds the so-called circumscribing rectangle BB (bounding box) of the image of the marker or marking. Even if a considerable percentage of the pixels of the marker or marking are missing, it interferes only a little with the result compared with background pixels erroneously classified as marker pixels.

The control loop 3 represented in FIG. 1 in the form of block diagrams finally terminates via the statistics processor $33_1$ following the classifier 32. A controller 34 and a robot control 11 are connected downstream of the processor $33_1$.

The center and the disparity are then determined from the image centers SP of the markers or markings in two successive images from the cameras $2_1$ and $2_2$. A deviation of the center from its set position in the center area of the monitor image is used for a lateral control (move up–down–left–right), and the deviation of the disparity from every set value is used for a transverse control (zoom in–out). In all cases the restoring speed is proportional to an amount of deviation.

In other words, the robot moves the laparoscope laterally (left/right, up/down) to keep the marker in the center of the images; and it moves optionally the laparoscope in and out (transverse or zooming direction) to keep the distance between the laparoscope-head and the surgical instrument. The two cameras are both aimed at a single convergence point at a certain distance from their lenses at the end of the laparoscope; if the marker is not at that distance, the center SP in the two stereo images will not correspond in position, but the images will be superimposed in position if the marker is at the convergence point.

The stability of the controlled system is assured by the lateral and transverse feedback control. Furthermore, the system is quiet in the vicinity of the working point, which is very important for the surgeon; but the system is rapidly restored in case of large amounts of deviation. That is (for example in the lateral control), the system corrects weakly or not at all for small deviations between the marker center point SP and the screen center; but if the marker starts to move close to the edge of the screen, then the degree of correction is increased. The effect for the surgeon is that the instrument can be moved freely in a limited space without the viewing pictures jiggling, but the viewing picture automatically tracks the marker when the marker moves too far away from the center of the viewing picture.

To increase the system dependability, the confidence in the measurements is continuously checked in a unit 36 performing confidence tests and a program control. For this purpose a contour data processor 35 is connected in parallel with the two statistics processors $33_1$ and $33_2$ connected downstream of the classifier 32. In the unit 36 performing the confidence tests and a program control, so-called regions of interest ROI (Region Of Interest), in which the image of a marker or marking is expected, are determined with the aid of the circumscribing rectangle BB delivered by the statistics processor $33_2$ and the contour formed by the contour processor 35, and are applied by the unit 36 to the controller 34 as well as to the two statistics processors 33, as shown by the arrows in FIG. 1. Pixels located outside the ROI are not evaluated.

It is furthermore necessary for a practical use of the method in accordance with the invention to determine what color the markers or markings are to have and how the classifier must be laid out in connection with a given marker or marking. For this purpose it is particularly necessary to determine how the LU table is to be laid out.

To solve these problems, the invention has been developed to include a color selection program with the aid of a graphics interface and in accordance with the principle of "monitored learning by means of examples". All that is required for applying this method is a computer with the capability of displaying color images in real colors and a mouse interface for drawing polygons on the monitor.

The core of the color selection method developed by the present inventor is a calculation of two-dimensional histograms in polygonal areas and a graphic representation of the results. In the graphic representation it is necessary to represent similar colors on points closely located near each other, so-called compact clusters, and unlike colors on points which are far apart, so-called disjunctive clusters.

A number of color images of typical scenes are taken from video tapes made of actual operations, in which all possible colors occurring in the course of such operations are contained. Each one of these images is stored in the RGB format, i.e. each pixel of the images has an RGB value representing a color. Since it is sufficient to represent each color by two values, each RGB value is projected on a two-dimensional plane, i.e. the HS plane, containing the shade of color (hue) and the color saturation (saturation). In the course of this the number of pixels which are projected on the same HS position is added together in each position of the HS plane. A two-dimensional color histogram is obtained by means of this, in which the frequency of occurrence of all colors in the scenes is represented.

A color histogram is represented to provide users with a graphic visual impression of the colors; in this case the color of each HS point has the average color intensity of all pixels registered in this point. A user is able to directly find existing color gaps (i.e. colors which do not appear during operations and so do not appear on the histogram), which can be used for color-coding the surgical instruments. The user can give the manufacturer objective color measurements (H, S) for this.

For the sake of safety, the marked instrument or surgical instruments are again color-analyzed in the course of a classification layout in a hardware implementation in case of a possible color change of the selected color by the camera.

In regard to the layout of the classifier 32, a user will therefore select the area whose colors later constitute a class by marking the so-called circumscribing polygons by means of the mouse. The calculation of the color histogram is limited to the interior of the polygons and the result is graphically represented. The user can then recognize the layout of the color clusters in this representation and he can fix the class limits, again by circumscribing polygons. In the process it is also possible to combine different colors in one class. The LU table 32-1 in the classifier 32 therefore receives the entry 255 only for the selected colors, as already explained above, while it receives the entry zero for all other colors.

Extensive research by the inventor has shown that the selection of a color exclusively in accordance with a subjective impression is difficult and can often lead to unsatisfactory results. The reason for this is that the color temperature of the illumination, the color reproduction of the camera and the color reproduction of the monitor lead to color shifts.

In addition, the same color seems to be differently perceived in different brightness. The above-described color selection method solves this problem since it is independent of color shifts of the cameras and the monitor and in this way makes the color selection and the outlay of the classifier more objective.

Furthermore, the above-described color selection method can be used for any type of color classification, for example for quality control of colored textiles. In this case it is then possible to tailor it to a defined color in order to control the course of the threads of this color or the printing of a pattern, for example.

It is furthermore advantageous that the user does not have to deal with numbers in any way. He can operate the color selection method in a very comfortable manner and achieve reliable results very quickly. It is furthermore possible to adapt the selectivity of the classifier to the respective problem in a very simple manner. In contrast to analytical classifiers or neural nets, there are no restrictions in regard to the form of the class limits.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. The means and materials for carrying out various disclosed functions may take a variety of alternative forms without departing from the invention. It is to be understood that the phraseology or terminology employed herein is for the purpose of description and not of limitation.

What is claimed is:

1. In connection with minimally invasive surgery, a method for tracking a surgical instrument with a mono-laparoscope located in an operating area and controlled by a robot and being movable relative to the surgical instrument; the surgical instrument being viewable by a camera producing one image visible on a monitor device having a center area; the method comprising the steps of:
    color-coding the surgical instrument with a marking;
    identifying the surgical instrument by the marking in one image provided by the camera;
    determining marking positions of the color-coded surgical instrument in the image;
    deriving control signals, for controlling the robot, from the marking positions;
    wherein the control signals cause the robot to automatically move the laparoscope toward a laparoscope position where the color-coded surgical instrument is shown in the center area of the monitor device.

2. The method in accordance with claim 1 wherein, in the step of deriving control signals, correction of the laparoscope position is relatively light when the instrument is shown near the center area of the monitor device, but stronger when the instrument is shown in an edge area outside the center area; whereby interfering movements when working with the surgical instrument are prevented.

3. In connection with minimally invasive surgery, a method for tracking a surgical instrument with a stereo-laparoscope located in an operating area and controlled by a robot and being movable relative to the surgical instrument; the surgical instrument being viewable by two cameras producing two respective images visible on a monitor device having a center area; the method comprising the steps of:
    color-coding the surgical instrument with a marking;
    identifying the surgical instrument by the marking in the images provided by the two cameras;
    determining marking positions of the color-coded surgical instrument in the images;
    deriving control signals, for controlling the robot, from the marking positions;
    wherein the control signals cause the robot to automatically move the laparoscope toward a laparoscope position where the color-coded surgical instrument is shown in the center area of the monitor device
    and to keep a constant distance between the laparoscope-head and the surgical instrument.

4. The method in accordance with claim 3, including sequential steps of:
    (a) transmitting the images in a RGB color format to an image processing unit (3) in which the images are converted to HSV color format;
    (b) enhancing the marking by setting marking values to a defined logic value and setting all non-marking values to a different logic value according to a pre-allocated look up (LU) table (32-1) of a classifier (32) of the image processing unit (3);
    (c) identifying marking pixels by statistical evaluation in a statistics processor ($33_1$, $33_2$) connected downstream of the classifier (32), the marking pixels including a marking image center (SP) and a marking image circumscribing rectangle (BB);
    (d) applying the marking pixels via a controller (34) to a control unit (11) of the robot (10), including the steps of:
    determining in the control unit (11), from one of the two camera images, a lateral deviation of the marking image center from a set position in the center area of the monitor device and
    using the lateral deviation for the lateral control of the robot-guided laparoscope; and
    determining in the control unit (11), from both of the camera images, a disparity of marking image centers of the two images, and
    using the disparity for the transverse control of the robot-guided laparoscope.

5. The method in accordance with claim 4, including the step of switching between the inputs of the cameras ($2_1$, $2_2$) at a predetermined frequency for generating pictures at the input of the image processing unit (3) by means of a multiplexer (30).

6. The method in accordance with claim 4, wherein:
    as the address for the LU table (32-1), a word with double the number of bits is formed in the LU table (32-1) of the classifier (32) from a number of bits of the color components "H" and "S" of the color images converted into the HSV space;
    the LU table (32) is pre-allocated in such a way that color values which are part of the marking receive the highest logical value and the remaining values are zero;
    for correcting pixels which were erroneously given the highest value, all pixels which are associated with a very low signal level corresponding to noise or a very high signal level corresponding to saturation are set to zero in that the components "V" of the converted color images are passed through a bilevel threshold value generator (32-2) and are multiplied with the output signal of the LU table (32-1) in a multiplication unit (32-3) and residual errors in the form of individual pixels or pixel groups are subjected to time and spatial filtering (32-4, 32-5) and are subsequently suppressed through a single-level threshold value generator (36-2).

7. The method in accordance with claim 4, wherein a continuous confidence check of measurements is performed for increasing system dependability.

8. The method in accordance with claim 4, wherein the method comprises steps of:

(a) presenting camera images on the monitor device by computer-assisted color analysis, marking regions on the images with the aid of an input device, evaluating interior areas of the regions to be further evaluated in view of the preparation of a two-dimensional color histogram in a color space of standardized brightness;

(b) representing on the monitor as a result a prepared two-dimensional color histogram, allowing marking of regions with the aid of the input device in the histogram representation, assigning an identification in the form of a number value to the region, and (c) subsequently automatically determining from the color regions marked in step (b) and the assigned identifications an allocation of a look up table, by means of which the identification selected in step (b) is assigned to each marked color of the two-dimensional color space.

9. The method in accordance with claim 8, wherein the input device is a mouse.

* * * * *